(12) United States Patent
Lukashevich

(10) Patent No.: US 9,360,932 B1
(45) Date of Patent: Jun. 7, 2016

(54) SYSTEMS AND METHODS FOR VIRTUALLY DISPLAYING REAL MOVEMENTS OF OBJECTS IN A 3D-SPACE BY MEANS OF 2D-VIDEO CAPTURE

(71) Applicant: Uladzislau Anatolievich Lukashevich, Minsk (BY)

(72) Inventor: Uladzislau Anatolievich Lukashevich, Minsk (BY)

(73) Assignee: INTELLECT MOTION LLC., Moscow (RU)

(*) Notice: Subject to any disclaimer, the term of this patent is extended or adjusted under 35 U.S.C. 154(b) by 0 days.

(21) Appl. No.: 13/900,551

(22) Filed: May 23, 2013

Related U.S. Application Data

(60) Provisional application No. 61/694,321, filed on Aug. 29, 2012.

(51) Int. Cl.
*G06F 3/03* (2006.01)
*G06F 3/01* (2006.01)
*A63B 24/00* (2006.01)
*A61B 5/11* (2006.01)

(52) U.S. Cl.
CPC .............. *G06F 3/011* (2013.01); *A61B 5/1127* (2013.01); *G06F 3/0325* (2013.01); *A63B 24/0006* (2013.01); *A63B 2024/0015* (2013.01)

(58) Field of Classification Search
CPC ............... A63B 24/00; A63B 24/0003; A63B 24/0006; A63B 24/0021; A63B 24/0087; A63B 2024/0009; A63B 2024/0012; A63B 2024/0015; A63B 2024/0025; A63B 2024/009; A63B 2024/0093; A63B 2024/0096; A61B 5/11; A61B 5/1114; A61B 5/1116; A61B 5/1127; A61B 5/6801–5/6807; G06F 3/014; G06F 3/0325; G06F 3/0304; G06F 3/011

USPC ......... 345/419; 482/142; 340/573.1; 375/240.08; 715/757; 73/379.04; 356/614; 348/207.99; 463/8
See application file for complete search history.

(56) References Cited

U.S. PATENT DOCUMENTS

| | | | |
|---|---|---|---|
| 7,492,268 B2 * | 2/2009 | Ferguson et al. | 340/573.1 |
| 7,583,252 B2 | 9/2009 | Kurtenbach | |
| 7,665,041 B2 * | 2/2010 | Wilson | G06F 3/017 715/860 |
| 7,782,361 B2 * | 8/2010 | Kotake et al. | 348/207.99 |
| 8,092,355 B2 * | 1/2012 | Mortimer et al. | 482/142 |
| 8,601,379 B2 * | 12/2013 | Marks et al. | 715/757 |
| 8,854,433 B1 * | 10/2014 | Rafii | G06F 3/017 348/42 |
| 2002/0183961 A1 * | 12/2002 | French et al. | 702/150 |
| 2003/0063292 A1 * | 4/2003 | Mostafavi | 356/614 |
| 2007/0043310 A1 | 2/2007 | Trandafir et al. | |
| 2007/0146484 A1 | 6/2007 | Horton et al. | |
| 2008/0045809 A1 | 2/2008 | Hermannsson | |

(Continued)

*Primary Examiner* — Dwayne Bost
*Assistant Examiner* — Darlene M Ritchie
(74) *Attorney, Agent, or Firm* — Transpacific Law Group; Pavel I. Pogodin

(57) ABSTRACT

The disclosed method is intended for virtually reproducing real movements of an individual by 2D measurement of positions of two markers one of which is located, e.g., on a body trunk and another is held in a hand. A human being is selected as an object for implementation of the method based on specificity of movements of the body parts as a reaction of the muscle-joint sense in response to the visual information obtained through the visual channel. Video catching is performed by detecting the detectable elements such as LEDs attached to the markers by means of a web camera with visual matrix, and processing the video catching in a CPU into movement of a single cursor on the display. The method may find use in fitness, gaming, simulation, manipulation of antropometric robots, sport, medicine, etc.

10 Claims, 4 Drawing Sheets

(56) References Cited

U.S. PATENT DOCUMENTS

| | | |
|---|---|---|
| 2008/0100825 A1 | 5/2008 | Zalewski |
| 2009/0033623 A1* | 2/2009 | Lin ........................ G06F 3/014 345/158 |
| 2009/0099480 A1 | 4/2009 | Salgo et al. |
| 2009/0163262 A1* | 6/2009 | Kang ............................... 463/8 |
| 2010/0176952 A1* | 7/2010 | Bajcsy et al. .............. 340/573.1 |
| 2010/0199228 A1* | 8/2010 | Latta ....................... G06F 3/011 715/863 |
| 2010/0329528 A1 | 12/2010 | Hajnal et al. |
| 2011/0096832 A1* | 4/2011 | Zhang et al. ............. 375/240.08 |
| 2011/0106305 A1 | 5/2011 | Brethe |
| 2011/0260890 A1 | 10/2011 | Larsen et al. |
| 2011/0301934 A1* | 12/2011 | Tardif ............................... 704/1 |
| 2011/0306422 A1* | 12/2011 | Nishimoto .............. A63F 13/06 463/36 |
| 2012/0108392 A1 | 5/2012 | Chu |
| 2013/0222246 A1* | 8/2013 | Booms ................... G06F 3/017 345/168 |
| 2015/0138086 A1* | 5/2015 | Underkoffler .......... G06F 3/017 345/158 |
| 2015/0294480 A1* | 10/2015 | Marks .................... G06F 3/017 463/31 |

* cited by examiner

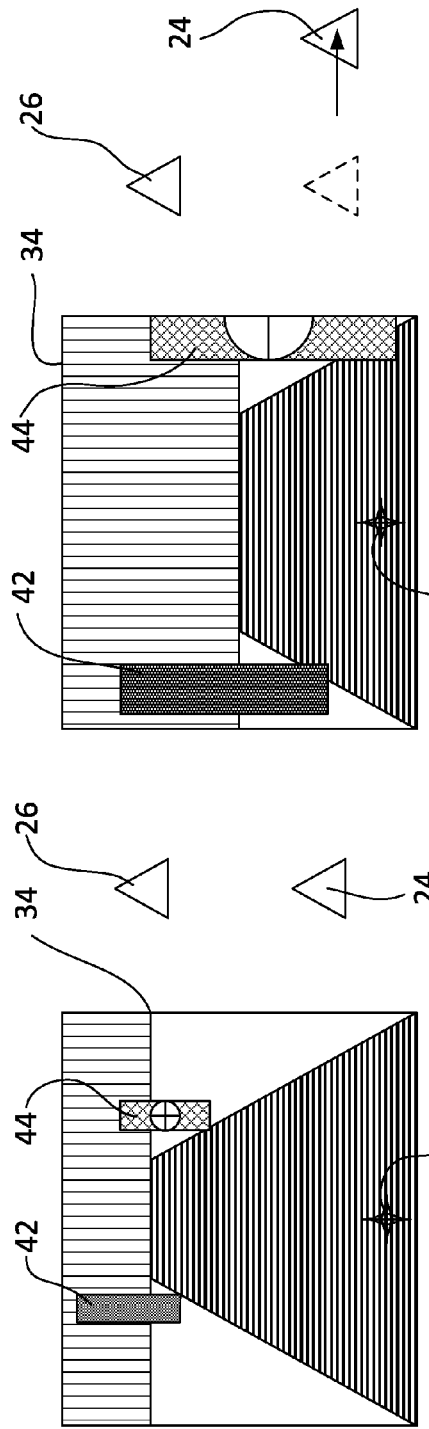
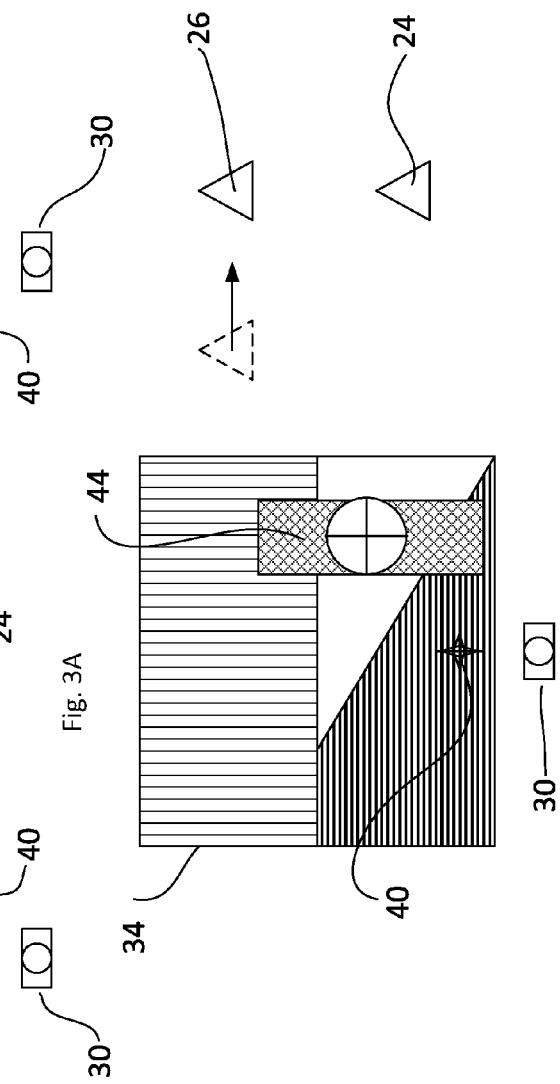
Fig. 3A
Fig. 3B
Fig. 3C

SYSTEMS AND METHODS FOR VIRTUALLY DISPLAYING REAL MOVEMENTS OF OBJECTS IN A 3D-SPACE BY MEANS OF 2D-VIDEO CAPTURE

CROSS-REFERENCE TO RELATED PATENT APPLICATIONS

This non-provisional patent application is based on and claims the benefit of priority from U.S. provisional patent application No. 61/694,321 filed on Aug. 29, 2012, the entire disclosure of which is incorporated by reference herein.

BACKGROUND OF THE INVENTION

1. Field of the Invention

The present disclosure relates to a method for virtually reproducing real movements of an object or objects by 2D measurement of positions of this object or objects, e.g., by means of 2D-video capture with the use of a web camera. More particularly, the method of the disclosure can be used for on-line registering, reproducing, and recording movements of human body parts, the dynamics of which depends on the human body structure, i.e., muscles, joints, etc. The proposed method may find use in fitness, gaming, simulation, manipulation of antropometric robots, sport and medicine, and namely in neurology, traumatology, orthopedics, pediatrics, gerontology, sports medicine, medical rehabilitation, or the like.

2. Description of the Related Art

Known in the art are many techniques and methods for recognizing and detecting spatial displacements of objects, based on different physical principles (magnetic field, sound and radio wave oscillation intensity of bioelectric potentials and so on) and their combinations. One of these methods is based on the principle of video capture. Video capture is a process of converting an analog video signal produced, e.g., by a video camera, to digital video signals. The resulting digital data are referred to as a digital video stream or simply video stream.

Methods and systems for conversion of 2D video data into 3D video data are known in the art. For example, US Patent Application Publication 20110096832 (Published in 2011, inventors Rong Zhang, et al.) discloses a depth map generation technique for conversion of 2D video data to 3D video data. The techniques may use a combination of motion and color considerations in the depth map generation process. For depth map initialization, initial depth values may be assigned to pixels of a video unit based on motion associated with the pixels relative to corresponding pixels of a previous video unit of a video sequence. Initial depth values that satisfy a threshold may then be adjusted, wherein the adjusted depth values are based on color associated with the pixels. An initialized depth map can then be generated for the video unit, wherein the initialized depth map comprises the initial depth values for a first subset of the pixels and the adjusted depth values for a second subset of the pixels. In some cases, the initialized depth map may be used as a final depth map without further processing, and in other cases, additional techniques may be applied with respect to the initialized depth map in order to define a final depth map.

Also known are methods and systems for monitoring and controlling motions and postures of a human body. For example, US Patent Application Publication 20120108392 (published in 2012, inventors Jeffrey Chu, et al. discloses an apparatus, system and method for fall prevention training that deliver, study, and analyze the biomechanics of a disturbance event, such as a slip or trip incident, so that an appropriate response can be executed by the person to reduce or eliminate the number of falls experienced. The apparatus includes a platform that delivers a disturbance event in less than about 500 ms and preferably in the range of about 100 ms to about 200 ms. The method includes a unique protocol for fall prevention training using the apparatus. The disturbance event can create instability in the joint of the individual. An individual's walking gait can be monitored with the portions thereof detected. A disturbance event can be triggered when a given portion of the walking gait is detected. Also, the disturbance even can be triggered manually, at preset intervals or according to preset script.

US Patent Application Publication 20100176952 (published in 2010, inventors: Ruzena Bajcsy, et al.), incorporated herein by reference, discloses an approach for determining motions of a body using distributed sensors. In one embodiment, an apparatus can include: a plurality of sensors coupled to a body, where each sensor is positioned at about a designated location on the body, and where each sensor is configured to acquire motion data related to movement of the designated location on the body and at which the sensor is positioned, and to reduce the motion data into compressed and transmittable motion data; and a base station configured to receive the compressed motion data via wireless communication from at least one of the plurality of sensors, the base station being further configured to remove outlier information from the received motion data, and to match the received motion data to a predetermined action, where the predetermined action indicates a movement of the body.

However, the methods described above and any other methods known to the applicants do not provide sufficient accuracy in virtual reproduction of real movements of a human body as an object since they do not take into account the response time and specificity of such movements.

SUMMARY OF THE INVENTION

The inventive methodology is directed to methods and systems that substantially obviate one or more of the above and other problems associated with conventional techniques for recognizing and detecting spatial displacements of objects.

It is known that one of the main functions of a human being is the ability to provide a certain constancy of body position in space through an adequate and accurate realization of motoring and coordination functions defining activity of the balance body system, e.g., postural system, including multimodal afferentation from various extra and inner receptor systems, multilevel hierarchically organized system of the integral analysis in the form of afferent synthesis, efferent synthesis system triggering the motor corrections by launching programs aimed at advancing reflection and realized in the form of reactive and proactive postural control, etc.

Any movement at the level of its programming involves creation of a determined biokinematic range—joint motions in certain angular ranges to achieve the assigned task. This process always includes the major joints as the main elements of biomechanical load distribution in dynamically changing body positions. Thus, the representative work of the postural system is to provide an adequate realization of postural strategy and to control extra environmental destabilizing factors by causing motor adaptation.

However, none of the existing systems of recognition and detection of spatial displacement of objects by converting 2D measurements into registered 3D data can implement the principle of spatial control and management of complex kinematics of a human body.

In the context of the present disclosure, a virtual movement in the 3D space means a movement of a virtual object, e.g., a cursor that describes the movement of real objects on the screen of the display. The movements of the real objects in the 3D space are understood as real movements.

In one or more embodiments, the method is based on finding of a method for virtual 3D reconstruction of complex kinematics of moving objects such as human body parts on the basis of captured 2D video data obtained by video recognition and/or detection of at least two isolated trigger markers.

In the proposed method, one of the markers is used for roughly controlling movements of the object in the direction of three main axes (X, Y, Z) of the 3D space, while another marker is used for finely controlling movements of the object via additional ongoing corrections of the general direction assigned by computer vision to the virtual object or cursor.

In one or more embodiments, the first marker has a function that describes linear movements in linear approximation, including uniformly accelerated and uniformly decelerated movements, while the second marker, in addition to the movements controlled by the first marker, incorporates a function that controls linear movements in combination with rotations and a direction of camera view assigned to the virtual object. Such a combination of linear movements with rotations will be referred to as "non-linear movements". In context of the present disclosure, the first marker will be referred to as "a coarse-movement control marker" and the second marker will be referred to as "a fine-movement control marker".

In the context of the disclosure, the method considers movements of a complex object such as a human body having a plurality of functionally related body parts that can move relative to each other, these movements can be classified as movements performed with different mobilities. For example, the human trunk has a certain range of mobility which is limited as compared to the range of mobility provided by a hand.

Since the method is intended for use of a human being as an object, the first marker may be allocated on a part of the body that has a limited mobility, e.g., on a lower part of the trunk, e.g., on the waste line, while the second marker may be attached to a part of the body that has a greater mobility, e.g., may be held in a hand.

In one or more embodiments, the functions of the first and second markers can be interchangeable. For exampled, in addition to or instead of the linear movements in the direction of axes X, Y, Z, the first marker may also incorporate a function for controlling rotation.

In one or more embodiments, the first and second markers are assigned various combinations of movement controlling functions selected from linear uniform, linear non-uniform, rotational uniform, and rotational non-uniform movements.

In one or more embodiments, the first and second markers can be installed on various moveable parts of the human body including, the head, shoulder, forearm, arm, wrist, hip, leg, foot, etc.

In view of the fact that the proposed method is based on a specificity of a human as an object, the most important information channels that control movements of the markers are: 1) a visual channel that allows to determine fine changes of the environment in the direction of movement in the form of dynamic control (assessment of the situation) and 2) a channel of a muscle-joint sense which allows to determine the current position of the body in real space based on relative positions of body parts in terms of dynamic control (balance of strains in muscles and ligaments).

In view of the above, in addition to the aforementioned markers, a system suitable for realization of the proposed method comprises a digital video-registering device such as a web camera that performs 2D video capture of marker movements and a central processing unit (CPU) that processes 2D video capture data and converts these data into a virtual 3D data that are reproduced on a display that performs a biofeedback of the body positions in a real space and near real time.

In the context of the present disclosure, the term "marker" designates a detectable element, i.e., any object that can be detected by a web camera. Such a detectable element may comprise, e.g., a signal generating means such as a light source or a group of light sources, a mirror or a group of mirrors, a characteristic part of a human body, a characteristic part of a human garment, or a characteristic object attached to a human garment, e.g., a badge or a button. The term "light source" may cover a single light source or a group of light sources.

Since the coarse movement marker performs mainly linear movements, i.e., movements along X,Y,Z axes in the orthogonal system of coordinates, in case if the individual assumes, e.g., a sitting position in which the coarse movement marker is practically immobile, this marker may comprise a single detectable element. Therefore, In one or more embodiments, the display may comprise a smart TV, and the individual may be in a sitting position and control movements of the cursor on the screen of the display by moving the fine movement marker that is held in a hand and contains at least three detectable elements. Accordingly, a coarse movement marker may be selected also from characteristic parts of a body, e.g., the nose, the lips, the eyes, or the like.

In view of the above, in the context of the present disclosure the term "allocated on a human body" covers not only attaching of the marker to the human body or to the garment but also allocating a detectable element as a characteristic part of the human body or the garment, e.g., the nose or a button.

In one or more embodiments, a marker may comprise a flat substrate that supports at least three signal-generating elements that may generate signals detectable by a respective visual sensor or sensors. These three signal generating elements lie in a common plane of the substrate surface and can be located, e.g., at apices of an imaginary triangular figure. The signal generating elements may comprise, e.g., LEDs operating in a visual or infrared wavelength range, mirrors with a source of external illumination, light micro-bulbs, etc.

On both markers, the signal generating elements may be identical or different. The markers, or their faces, in turn, may be identical or may have different geometrical shapes and dimensions. The markers has means for attachment to the objects, i.e., to the human body or clothes. Such marker attachment means may comprise, e.g., so called "flexible touch fasteners. Such fastener systems are commercially available from VELCRO® (Velcro, Manchester N.H.), Minnesota Manufacturing & Mining Co. (3M SCOTCH-MATE™), and DURAGRIP™. The general construction of the fastener system is comprised of a soft fuzzy material (Loop) side and a rougher (Hook) side. When pushed together, hundreds of tiny hooks engage the loops to form a strong fastener. Alternatively, there are systems that have a male/female design where the male "lollipop" fits securely into a corresponding female site where the lollipop is engaged by the female portion. Other attachment means may comprise buttons, snapping buttons, pins, etc.

The marker, which is intended for allocation on a body part that possesses higher mobility, e.g., the marker that is to be held in a hand, may have a shape convenient for grasping in a hand.

A web camera or cameras may comprise a conventional web camera/cameras that is/are intended for video capture and for generation of 2D video capture data to be transmitted to the CPU of the system. The web camera is installed in a position in which both markers can be caught by the web camera within the range of interest, i.e., within the range of movements of the human body parts to which the markers are attached.

The CPU, which may comprise a conventional personal computer, receives the 2D video capture data flow from the web camera and processes these data flow by means of an algorithm that makes it possible to identify the data obtained from each marker. The captured 2D signals obtained by the signal processing unit are processed in such a manner that makes it possible to reproduce 3D motions of the virtual object and its parts in real time as well as camera vision for the virtual object in a virtual space.

The display for virtual reproduction of real movements of the depicted object or parts of the object may comprise a conventional digital display that may represent computer video signals or TV video signals.

The method is implemented as follows. A person (a participant of a game or a patient who is subject to a medical treatment, e.g., to rehabilitation of an injured hand, or any other individual to whom the method can be applied) may be used as an object whose motion or motions of body parts are to be reproduced on the display screen. The first marker is attached, e.g., to a body part that possesses a limited mobility, e.g., to the lower part of the body trunk, and the second marker is attached to the body part that possesses high mobility, e.g., is held in a hand. If the markers generate active video signals, e.g., by emitting light of LEDs, they are activated for generating visual signals susceptible by the markers.

Next, the web camera is switched on, and the field of vision of the camera is adjusted so that the entire range of the controlled body parts falls into the vision of the chamber. The web camera is connected to the CPU, and the latter is activated for operation in a selected mode (real-time mode or/and data-recording mode).

The system is ready for realization of the method. For example, let us assume that an object is an injured hand of a person and that the treatment is rehabilitation of the hand movements. The treatment consists of a set of exercises such as swinging motions of the injured hand from a certain initial point seen on the screen of the display to a certain target point on the same screen. The person moves the marker-holding body parts to positions convenient for starting the treatment. According to the method, both markers are seen on the screen as one common point, i.e., a cursor. After the initial position is achieved, e.g., by moving the first marker forward, back, to the left, or to the right, the injured hand treatment is started by moving the hand linearly or rotationally, or with combination of both movements, as may be prescribed by a physician or another appropriate medical specialist, or the like. Of course, if the procedure requires, both markers can be moved simultaneously and, if necessary, the procedure may be recorded for subsequent analysis or for measuring positions of the cursor, and hence of the respective marker, relative to the initial point.

From the viewpoint of functionality of human body parts as moveable objects used for realization of the proposed method, the events described above can be considered as follows:

Through the visual analyzer, i.e., the human vision, a virtual event taking place on the monitor screen determines motivation that starts the motor program, namely the direction of movement of the body parts. Direct initiation of the motor program is based on the state of the "internal body scheme".

The internal body scheme is a matrix that determines the functional capacity of kinematic links of the body. The "internal model of the body" is formed mainly due to information obtained from polymodal receptors of the muscles and tendons. At the level of its cognitive analysis, the incoming visual information activates the motivational component of the motor program and is superimposed on the "internal model of the body," eventually forming a motor strategy of the body in a functionally adapted mode.

A motor program is an abstract representation of movement that centrally organizes and controls many degrees of freedom involved in performing an action. Signals transmitted through efferent and afferent pathways allow the central nervous system to anticipate, plan or guide the movement. Evidence for the concept of motor programs includes the following:

1) Processing of afferent information (feedback) is too slow for on-going regulation of rapid movements.

2) Reaction time (time between "go" signal and movement initiation) increases with movement complexity, suggesting that movements are planned in advance.

3) Movement is possible even without feedback from the moving limb.

4) This is not meant to underestimate the importance of feedback information, merely that another level of control beyond feedback is used.

5) Before the movement as information about initial position, or perhaps to tune the spinal apparatus.

6) During the movement, when it is either "monitored" for the presence of error or used directly in the modulation of movements reflexively.

7) After the movement to determine the success of the response and contribute to motor learning.

At the level of the internal model, the motions of different parts of the body (anatomical links) are coordinated around those parts of the body on which the markers are mounted. As a result, the individual performs a purposeful action in the form of an appropriate response to the elapsed virtual event.

Thus it is shown that the proposed method is unique in that it is applied to a human being as an object that carries coarse-movement and fine-movement markers and performs spatial movements registered with a 2D video capture and virtually shown on the screen of the display.

In accordance with one aspect of the embodiments described herein, there is provided a computer-implemented method for virtually displaying real movements of objects in a 3D-space by means of 2D-video capture, the method being performed in connection with a system comprising: at least a first marker and a second marker, both markers having detectable elements laying in planes; a web camera that has a visual-matrix sensor that detects the detectable elements for creating a 2D video capture information about movements of said first marker and second marker, the visual-matrix sensor having a visual matrix having a plane with a pixel coordinate system onto which the images of the detectable elements are projected; a display having a display screen with an image of at least one target; and a central processing unit that communicates with the web camera and with the display and that processes the 2D capture information into 3D video capture signals, the method comprising: providing an object having at least a first part having a predetermined mobility and a second part having greater mobility than the predetermined mobility of the first part, both parts being independently moveable; allocating a first marker on the first part and the second marker on the second part of the object; arranging the first part and the second part in positions where the first marker and the second marker fall into vision field of the web camera; moving the first part and a second part with respective markers in space in an $X_1, Y_1, Z_1$ coordinate system, where axes $X_1$ and $Y_1$ form an $X_1$-$Y_1$ plane parallel to the plane of the respective marker, and axis $Z_1$ is directed from the $X_1$-$Y_1$ plane toward the visual-matrix sensor of the web camera; performing video catching of the movements of the first marker and of the second marker by detecting the detectable elements of the first marker and the second marker thus producing video catching information; sending the video catching information to the central processing unit and processing the video catching information by converting the movement of the first marker and the second marker into movement of a single cursor on the display; and moving the parts of the object with markers for placing the cursor to a desired position relative to the target.

In accordance with another aspect of the embodiments described herein, there is provided a computer-implemented method for virtually displaying real movements of an individual having a first body part of a predetermined mobility and a second body part having mobility higher than the predetermined mobility of the first body part, the individual performing real movements in a 3D-space, the method being performed in connection with a system comprising: at least a first marker and a second marker, both markers having detectable elements located on each marker in predetermined positions unchangeable with respect to the marker; a web camera that has a visual-matrix sensor that detects the detectable elements for creating a 2D video capture information about movements of said first marker and second marker, the visual-matrix sensor having a visual matrix having a plane with a pixel coordinate system onto which the images of the detectable elements are projected; a display having a display screen with an image of at least one target; and a central processing unit that communicates with the web camera and with the display and that processes the 2D capture information into 3D video capture signals, the method comprising: providing allocating a first marker on the first part and the second marker on the second part of the object; arranging the first part and the second part in positions where the first marker and the second marker fall into vision field of the web camera; moving the first body part and a second body part with respective markers in space in an $X_1, Y_1, Z_1$ coordinate system, where axes $X_1$ and $Y_1$ form an $X_1$-$Y_1$ plane parallel to the plane of the respective marker, and axis $Z_1$ is directed from the $X_1$-$Y_1$ plane toward the visual-matrix sensor of the web camera; performing video catching of the movements of the first marker and of the second marker by detecting the detectable elements of the first marker and the second marker thus producing video catching information; sending the video catching information to the central processing unit and processing the video catching information by converting the movement of the first marker and the second marker into movement of a single cursor on the display; and moving the parts of the object with markers for placing the cursor to a desired position relative to the target.

Additional aspects related to the invention will be set forth in part in the description which follows, and in part will be obvious from the description, or may be learned by practice of the invention. Aspects of the invention may be realized and attained by means of the elements and combinations of various elements and aspects particularly pointed out in the following detailed description and the appended claims.

It is to be understood that both the foregoing and the following descriptions are exemplary and explanatory only and are not intended to limit the claimed invention or application thereof in any manner whatsoever.

BRIEF DESCRIPTION OF THE DRAWINGS

The accompanying drawings, which are incorporated in and constitute a part of this specification exemplify the embodiments of the present invention and, together with the description, serve to explain and illustrate principles of the inventive technique. Specifically:

FIG. 1A is an initial position of the individual and markers attached to the body trunk and held in the hand of the individual relative to the web camera and FIG. 1B is a new position of the individual with markers relative to the web camera.

FIGS. 3A, 3B, and 3C illustrate positions of the cursors relative to the targets on the screen of the display, where FIG. 3A corresponds to an initial position of the cursor, FIG. 3B corresponds to the position of the cursor when the coarse-movement marker is moved forward; and FIG. 3C corresponds to the position of the cursor when the fine-movement marker is moved to the right from the position shown in FIG. 3B.

DETAILED DESCRIPTION

Figure 1A:
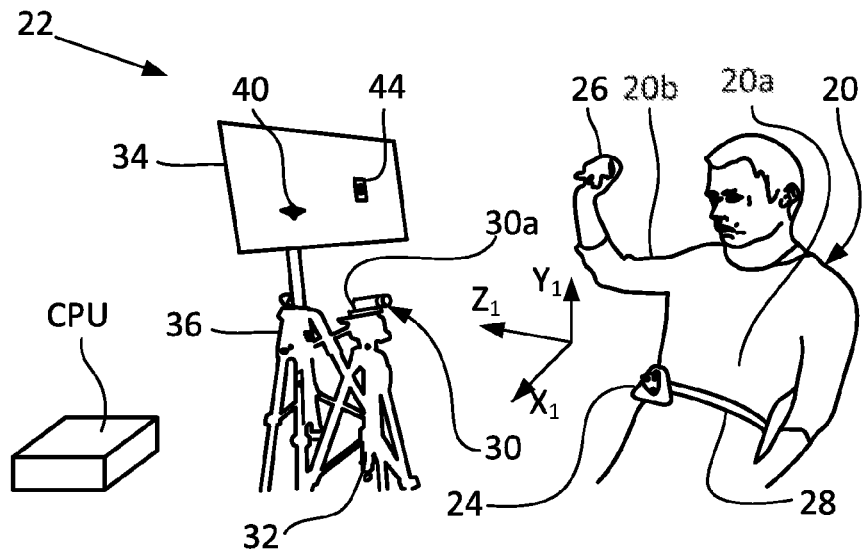
FIGS. 1A and 1B show exemplary positions of the markers on the body and in the hand of the individual during realization of the proposed method. Specifically.

In the following detailed description, reference will be made to the accompanying drawing(s), in which identical functional elements are designated with like numerals. The aforementioned accompanying drawings show by way of illustration, and not by way of limitation, specific embodiments and implementations consistent with principles of the present invention. These implementations are described in sufficient detail to enable those skilled in the art to practice the invention and it is to be understood that other implementations may be utilized and that structural changes and/or substitutions of various elements may be made without departing from the scope and spirit of present invention. The following detailed description is, therefore, not to be construed in a limited sense. Additionally, the various embodiments of the invention as described may be implemented in the form of a software running on a general purpose computer, in the form of a specialized hardware, or combination of software and hardware.

The present disclosure relates to a method for virtually reproducing real movements of an object or objects by 2D measurement of positions of this object or objects, e.g., by means of 2D-video capture with the use of a web camera.

The proposed method is based on the specificity of a human as an object having a visual channel that obtains visual information and a channel of a muscle-joint sense; the first part is a body part other than a hand, and the second part is a hand; the human is selected based on specificity of a movements of body parts as a reaction of the muscle-joint sense in response to the visual information obtained through the visual channel.

More particularly, the method of the disclosure can be used for on-line registering, reproducing, and recording movements of parts of a human body, the dynamics of which depends on the human body structure, i.e., muscles, joints, etc. Thus, a body trunk possesses mobility lower than a hand, and characteristic of the human body is also used as a basis for the proposed method.

The proposed method may find use in games, simulators, robot control systems, fitness, sport and medicine, and namely in neurology, traumatology, orthopedics, pediatrics, gerontology, sports medicine, medical rehabilitation, or the like.

In the context of the present disclosure, the term "marker" designates a detectable element, i.e., any object that can be detected by a web camera. Such a detectable element may comprise, e.g., a light source, a mirror, a characteristic part of a human body, a characteristic part of a human garment, or a characteristic object attached to a human garment, e.g., a badge or a button. The term "light source" may cover a single light source or a group of light sources.

Since the coarse movement marker performs mainly linear movements, i.e., movements along X,Y,Z axes in the orthogonal system of coordinates, in case if the individual assumes, e.g., a sitting position in which the coarse movement marker is practically immobile, this marker may comprise a single detectable element. Therefore, In one or more embodiments, the display may comprise a smart TV, and the individual may be in a sitting position and control movements of the cursor on the screen of the display by moving the fine movement marker that is held in hand and contains at least three detectable elements. Accordingly, a coarse movement marker may be selected not only from the detectable elements that can be attached to a human body or to the garment but merely a characteristic part of a body, e.g., the nose, the lips, the eyes, or the like.

In view of the above, in the context of the present disclosure the term "allocated on a human body" covers not only attaching of the marker to the human body or to the garment but also allocating a detectable element as a characteristic part of the human body or the garment, e.g., the nose or a button.

Although the method will be described below in application to a specific embodiment that involves the use of both markers in the form of three detectable elements located on the apices of an imaginary triangular body, it is understood that the method is not limited by this example and that the aspects mentioned with regard to the markers and movements are covered by any modifications within the scope of the claims attached hereinafter.

Figure 1B:
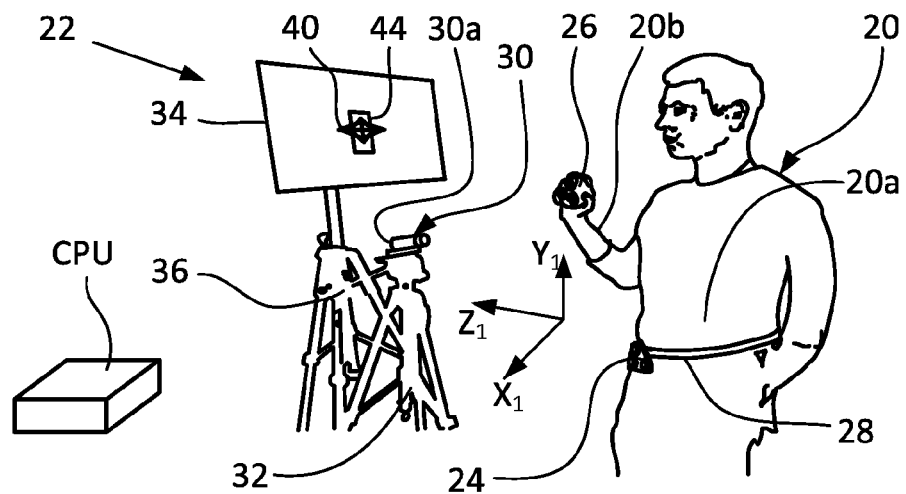

FIG. 1 shows a system 22 for realization of the proposed method with exemplary positions of the markers on the body and in the hand of the individual 20 during realization of the proposed method, wherein FIG. 1A shows an initial position of the individual 20 with a coarse-movement marker 24 attached to the body trunk 20*a* and a fine-movement marker 26 held in the hand 20*b* of the individual 20 relative to a web camera 30; and FIG. 1B is a new position of the individual 20 with the markers 24 and 26 relative to the web camera 30.

In FIGS. 1A and 1B, reference numeral 20 designates an individual for whom the proposed method is to be applied. Such an individual may comprise, e.g., a game participant, a patient treated for rehabilitation of a body part, a sportsman who executes certain moves, etc.

In the case shown in FIGS. 1A and 1B, the marker 24 is attached to a body part 20*a* that has low mobility, e.g., to a waist belt 28 on the belt ring of the individual 20, while the marker 26 is held in the right hand 20*b* of the individual 20.

As mentioned above, in the context of the disclosure, the method considers movements of a complex object, i.e., a human body of the individual 20 having a plurality of functionally related body parts that can move relative to each other, these movements can be classified as movements performed with different mobilities. For example, the human trunk has a certain range of mobility, which is limited as compared to the range of mobility provided by a hand.

The reason for which the applicants divided the markers into marker 24 for controlling movements of a low-mobility body part (hereinafter referred to as a "coarse-movement marker") and the marker 26 (hereinafter referred to as a "fine-movement marker") for controlling movements of a high-mobility body part is explained below.

Through the visual analyzer, i.e., the human vision, a virtual event taking place on the monitor screen determines motivation that starts the motor program, namely the direction of movement of the body parts. Direct initiation of the motor program is based on the state of the "internal body scheme".

The internal body scheme is a matrix that determines the functional capacity of kinematic links of the body. The "internal model of the body" is formed mainly due to information obtained from polymodal receptors of the muscles and tendons. At the level of its cognitive analysis, the incoming visual information activates the motivational component of the motor program and is superimposed on the "internal model of the body," eventually forming a motor strategy of the body in a functionally adapted mode.

A motor program is an abstract representation of movement that centrally organizes and controls many degrees of freedom involved in performing an action. Signals transmitted through efferent and afferent pathways allow the central nervous system to anticipate, plan or guide movement. Evidence for the concept of motor programs was described above in Items 1) to 7) of the "Summary".

At the level of the internal model, the motions of different parts of the body (anatomical links) are coordinated around those parts of the body on which the markers are mounted. As a result, the individual performs a purposeful action in the form of an appropriate response to the elapsed virtual event.

In view of the above, In one or more embodiments, the coarse-movement marker 24 has a function that describes linear movements in linear approximation, including uniformly accelerated and uniformly decelerated movements, while the fine-movement marker 26, in addition to the movements controlled by the first marker 24, incorporates a function that controls linear movements in combination with rotations. Such a combination of linear movements with rotations will be referred to as "non-linear movements".

In addition to the markers 24 and 26, a system 22 for realization of the method comprises a web camera 30 installed on an adjustable tripod 32, and a display 34 that may be attached to the wall or installed on a separate tripod 36 (FIGS. 1A and 1B). Alternatively, the individual 20 may be in a sitting position, and the display 34 may comprise a "smart" TV. The function of the web camera 30 is to detect positions of the detectable elements for creating 2D video capture information about movements of the first and second markers 24 and 26, respectively. As mentioned above, a detectable element may comprise a signal generating means or just a part of a body or garment detectable by the web camera. The web camera 30 contains a visual-matrix sensor 30*a* and an optical system (not shown) that builds an image of the individual 20 with the markers 24 and 26 on the matrix 32*a* of the sensor 30a. In other words, the visual matrix system shown in FIG. 4 has a pixel coordinate onto which the images of the detectable elements are projected. It is obvious that the image on the matrix of the sensor is reduced as compared to the original. The scale of the image on the matrix 32a is defined by a pitch between two neighboring pixels on the visual-matrix sensor 30a.

The matrix 32a of the visual sensor 30a can be associated with a certain pixel coordinate system X, Y, Z in the aforementioned scale. In the system X, Y, Z, the axes X and Y lay in the matrix plane while axis Z (not shown in the drawings) has the same scale as the scales on the axes X and Y.

Another indispensible component of the system 22 is a central processing unit (hereinafter referred to as a "CPU") that may comprise a conventional personal computer and is intended for controlling virtual displaying of real movements of the objects (in this case of the markers 24 and 26) in a 3D-space by means of 2D-video capture. In fact, the video capture comprises formation of an image on visual-matrix sensor 30a and transmission of the visual-matrix sensor signals with a predetermined frequency to the CPU for further processing.

The CPU processes the obtained visual-matrix sensor signals in accordance with an algorithm, which will be presented below in the description of realization of the method.

In the proposed method, the coarse movement marker 24 is used for roughly controlling movements of the body trunk of the individual 20 in the direction of three main axes ($X_1, Y_1, Z_1$) (FIGS. 1A and 1B) of the 3D space, while the fine-movement marker 26 is used for finely controlling movements of the object in the direction of the same axes ($X_1, Y_1, Z_1$).

In one or more embodiments, the coarse-movement marker 24 has a function that describes linear movements in linear approximation, including uniformly accelerated and uniformly decelerated movements, while the fine-movement marker 26, in addition to the movements controlled by the first marker 24, incorporates a function that controls linear movements in combination with rotations. Such a combination of linear movements with rotations will be referred to as "non-linear movements".

In one or more embodiments, the functions of the first and second markers can be interchangeable. For example, in addition to or instead of the linear movements in the direction of axes X, Y, Z, the coarse-movement marker 24 may also incorporate the function for controlling rotation.

In one or more embodiments, the coarse-movement marker 24 and the fine-movement marker 26 are assigned various combinations of movement controlling functions selected from linear uniform, linear non-uniform, rotational uniform, and rotational non-uniform movements.

In one or more embodiments, the coarse-movement marker 24 and the fine-movement marker 26 can be installed on body parts other than those shown in FIGS. 1A and 1B, e.g., on the head, shoulder, forearm, arm, wrist, hip, leg, foot, etc. In this connection, it is understood that such body parts as the lower part of the body trunk and the right hand are shown only as an example.

Figure 2:
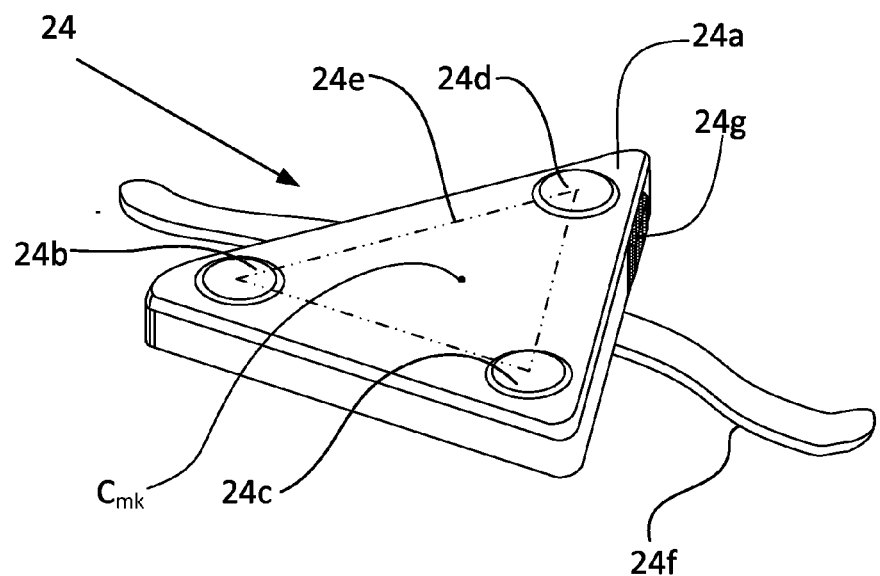
FIG. 2 is a view illustrating an exemplary embodiment of a marker suitable for the proposed method.

FIG. 2 is a view illustrating an example of a marker suitable for the proposed method. The markers 24 and 26 may be identical or different and may be embodied in various shapes and dimensions that are to be selected to match the conditions for realization of the method.

Since in the illustrated example both markers 24 and 26 are identical, only one of them, e.g., the marker 24, will be considered below. However, the shapes, dimensions and faces of the markers may be different. FIG. 3C corresponds to the position of the cursor when the fine-movement marker is moved to the right from the position shown in FIG. 3B.

In the context of the illustrated embodiment, the term "marker" designates a flat substrate 24a that supports at least three signal-generating elements 24b, 24c, and 24d that may generate signals detectable by the visual-matrix sensor 30a of the web camera 30 (FIGS. 1A and 1B). In the illustrated example, these three signal generating elements 24b, 24c, and 24d lay in a common plane of the substrate surface and are located at equal distances from each other, e.g., at apices of a triangular FIG. 24e. The signal generating elements 24b, 24c, and 24d may comprise, e.g., LEDs, operating in a visual or infrared wavelength range, mirrors with a source of external illumination, light micro-bulbs, etc.

In one or more embodiments, on both markers 24 and 26, the signal generating elements 24b, 24c, and 24d may be identical or different. The markers are provided with attachment means 24f for attachment to the objects, i.e., to a human body or clothes. Such marker attachment means 24f may comprise, e.g., so called "flexible touch fasteners". Such fastener systems are commercially available from VELCRO® (Velcro, Manchester N.H.), Minnesota Manufacturing & Mining Co. (3M SCOTCHMATE™), and DURAGRIP™. The general construction of the fastener system is comprised of a soft fuzzy material (Loop) side and a rougher (Hook) side. When pushed together, hundreds of tiny hooks engage the loops to form a strong fastener. Alternatively, there are systems that have a male/female design where the male "lollipop" fits securely into a corresponding female site where the lollipop is engaged by the female portion. Other attachment means may comprise buttons, snapping buttons, pins, etc.

In one or more embodiments, the fine-movement marker 26, which is to be held in a hand may have a shape convenient for grasping.

In one or more embodiments, the web camera 30 or cameras may comprise a conventional web camera/cameras that is/are intended for video capture and for generation of 2D video capture data to be transmitted to the CPU of the system. The web camera 30 is installed in a position in which both markers 24 and 26 can be caught by the visual-matrix sensor 30a of the web camera 30 within the zone of interest, i.e., within the range of movements of the human body parts to which the markers 24 and 26 are attached. The display 34 for virtual reproduction of real movements of the depicted object or parts of the object may comprise a conventional digital display that may represent computer video signals or TV video signals.

In one or more embodiments, the CPU, which may comprise a conventional personal computer, may have a wired or wireless communication with the web camera 30 and the display 34, receives a visual data flow from the visual-matrix sensor 30a of the web camera 30, and processes the data flow. The captured visual-matrix sensor signals obtained by the signal processing unit are processed in such a manner that makes it possible to reproduce 3D motions of the markers in the form of a single common cursor 40 (FIGS. 3A to 3C).

In one or more embodiments, transformation of the visual-matrix sensor signals into the single common cursor 40 that is shown on the screen of the display 34 is carried out in the CPU with participation of an algorithm that converts presentation of the visual-matrix sensor signals from a 2D system into a virtual 3D system.

In one or more embodiments, positions of the cursor 40 relative to the targets 42 and 44 on the screen of the display 34 are shown in FIGS. 3A, 3B, and 3C, where FIG. 3A corresponds to an initial position of the cursor 40, FIG. 3B corresponds to the position of the cursor 40 when the coarse-movement marker 24 (FIG. 1), is moved forward; and FIG. 3C corresponds to the position of the cursor 40 when the fine-movement marker 26 (FIG. 1) is moved to the right from the position shown in FIG. 3B.

The method can be realized in the form of the exemplary stages described below.

Figure 4:
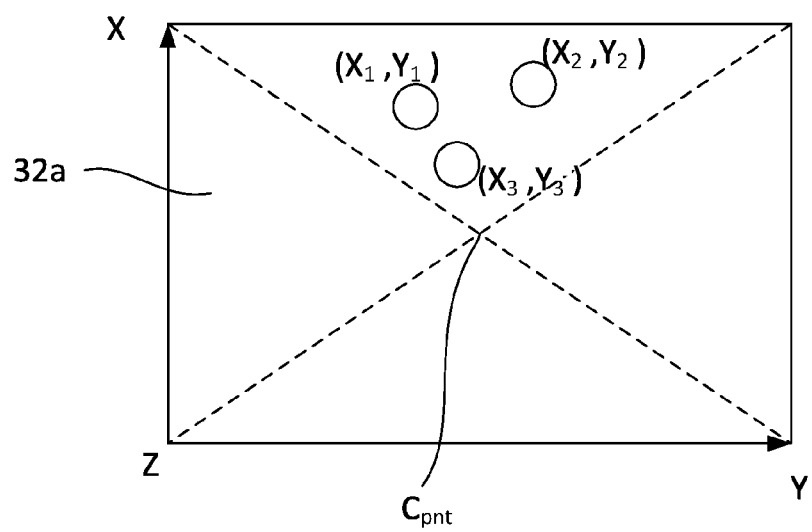
FIG. 4 illustrates an exemplary pixel coordinate system with coordinates of signal generating means on one of the markers.

For simplicity of understanding of the method, let us assume that the signal generating means are detectable elements located on each marker in predetermined positions unchangeable with respect to the marker. Let us assume for convenience that light generating means 24b, 24c, and 124d of each marker comprise, e.g., LEDs that are positioned on the apices of the triangle 24e (FIG. 2). When the marker 24 moves forward or back in the direction of axis Z with respect to the visual-matrix sensor 30 (FIGS. 1A and 1B, the distances between the apices of the triangle 24e in the plane of the matrix 32a (FIG. 4) change, and these changes are used for determining coordinates of the marker on the Z axis. If the matrix is turned from the X-Y plane, the ratio between the projection of the apices on the matrix changes, and these changes can be presented as turns of the marker 24 from the aforementioned plane X-Y. The term "3D movement in a virtual space" has to be construed in the context of the definition given above. The current coordinates x, y, and z of the three signal generating means in the course of such movements can be obtained with the use of the algorithm shown below. FIG. 4 is a picture illustrating the pixel coordinate system with coordinates of signal generating means on one of the markers.

$$d_1 = (X_1 - X_2)^2 + (Y_1 - Y_2)^2$$

$$d_2 = (X_2 - X_3)^2 + (Y_2 - Y_3)^2$$

$$d_3 = (X_3 - X_1)^2 + (Y_3 - Y_1)^2$$

$$l = \sqrt{\frac{d_1 + d_2 + d_3 \pm \sqrt{2 \ast ((d_1 - d_2)^2 + (d_1 - d_3)^2 + (d_3 - d_2)^2)}}{3}}$$

$$Z_{scale} = \frac{2 \ast \text{Distance}}{X_{scale} + Y_{scale}}$$

$$z = \frac{z_{scale}}{l}$$

$$X_{center} = \frac{X_1 + X_2 + X_3}{3}$$

$$Y_{center} = \frac{Y_1 + Y_2 + Y_3}{3}$$

$$x = \left(X_{center} - \frac{\text{width}}{2}\right) \ast \left(\frac{z}{X_{scale}}\right)$$

$$y = \left(Y_{center} - \frac{\text{height}}{2}\right) \ast \left(\frac{z}{Y_{scale}}\right)$$

where
the matrix 32a of the visual-matrix sensor 30 is associated with a certain pixel coordinate X, Y, Z system in the aforementioned scale (the Z axis is not needed in FIG. 4 as it is perpendicular to the plane of the drawing). In the X, Y, Z system, the axes X and Y lay in the matrix plane, and the axis Z is perpendicular to the X-Y plane and has the same scale as the scale on the axes X and Y.

d1, d2, and d3—distances from the signal generating means to the center of the visual matrix;

Xcenter and Ycenter—X, Y coordinates [in this case 0, 0] of the center of the visual matrix;

$X_1, Y_1$—coordinates of center of light #1 on camera image in camera's matrix coordinate system in pixels, for example 231.45 px, 374.09 px.

$X_2, Y_2$—coordinates of center of light #2.

$X_3, Y_3$—coordinates of center of light #3.

width—Horizontal resolution of camera matrix in pixels, for example 640 px.

height—Vertical resolution of camera matrix in pixels, for example 480 px.

Distance—is a distance between lights in meters, for example 0.05 meters.

Xscale—shows how many pixels would be in a stick with length 1 meter and located in 1 meter in front of the camera and oriented parallel of axis X.

Yscale—shows how many pixels would be in a stick with length 1 meter and located in 1 meter in front of the camera and oriented parallel of axis Y.

Zscale—a coordinate of the respective signal generating means on the Z axis.

x,y,z—Coordinates of center of lights in real world coordinates, where point (0, 0, 0) is a center of camera's matrix, axis Z is normal of camera's matrix, axis X and Y has same direction as camera's matrixes axis.

The method further comprises the step of selecting an arbitrary point Pa on each marker as a point of marker that is in a constant position relative to the marker and the detectable elements of the marker.

Let us assume that the center of the visual matrix 32a is a center point $C_{pnt}$ of the matrix 32a for subsequent calculations. The pixel coordinates of the points Pa of both markers 24 and 26 relative to the center point $C_{pnt}$ of the visual matrix are determined and sent to the CPU for calculating the coordinates of the points of markers with the use of the aforementioned algorithm. These calculations are performed with a predetermined frequency for obtaining trajectories of movement of both points of markers in the pixel coordinates of the visual matrix. The pixel coordinate system of the visual matrix 30a is then used as a common coordinate system for forming motion vectors from the center point of the matrix coordinate system to the current point on the trajectory of movement of the points of markers. The motion vectors of the points of markers are converted into a common vector, and the movement of the common vector is assigned to the cursor on the screen of the display so that the movements of the first and the second markers are presented on the screen of the display as movements of the cursor relative to the target.

Example of Treatment

An example of implementation of the proposed method is shown as treatment of the right hand of the individual for rehabilitation of mobility of the hand treated after an injury.

The individual 20 (a subject of a medical treatment, e.g., rehabilitation of an injured hand, or any other individual to whom the method can be applied) may be used as an object whose motion or motions of body parts of whom are to be reproduced on the display screen. The coarse-movement marker 24 is attached, e.g., to the lower part of the body trunk of the individual 20 who is sitting on a chair, and the fine-movement marker 26 is held in the right hand of the individual 20. If the markers generate active light signals, e.g., by emitting light from LEDs, they are activated for generating light signals susceptible by the video camera 30.

Next, in one or more embodiments, the web camera 30 is switched on, and the field of vision of the camera 30 is adjusted so that the entire range of the controlled body parts falls into the vision of the camera 30. The web camera 30 is connected to the CPU, and the latter is activated for operation in a selected mode (real-time mode or/and data-recording mode).

The system 22 is ready for realization of the method. For example, let us assume that an object is an injured hand 20b of the individual 20 (FIGS. 1A and 1B), and that the treatment is rehabilitation of the hand movements. The treatment consists of a set of exercises such as swinging motions of the injured hand 20b from a certain initial point seen on the screen of the display as the position of the cursor 40 shown in FIG. 3A to a certain target 44 on the same screen. The person moves the marker-holding body parts, e.g., the body trunk, and hence the marker 24, to a position convenient for starting the treatment. As mentioned above, both markers 24 and 26 are seen on the screen as one point, e.g., the cursor 40.

In one or more embodiments, after the position of the cursor 40 shown in FIG. 3B is achieved, e.g., by moving the first marker 24 forward, back, to the left, or to the right, the injured hand treatment is started by moving the hand, and hence the fine movement marker 26 (FIGS. 1A and 1B), linearly or rotationally, or with combination of both movements, as may be prescribed by a physician or another appropriate medical specialist, or the like, to the target position shown in FIG. 3C. If necessary, the procedure may be recorded for subsequent analysis or for measuring positions of the cursor, and hence of the respective marker, relative to the initial point.

All treatment procedure moves are accompanied by CPU data processing steps described above.

From the viewpoint of functionality of a human body parts as moveable objects used for realization of the proposed method, the events described above can be considered as follows:

Through the visual analyzer, i.e., the human vision, a virtual event taking place on the monitor screen 34 determines motivation that starts the motor program, namely the direction of movement of the body parts. Direct initiation of the motor program is based on the state of the "internal body scheme".

It is understood that the examples and drawings described herein should not be construed as limiting the application of the invention. For example, an object may comprise a robot that has at least two moveable body parts having different mobility as provided by a program. The markers may have dimensions and configurations different from those described in the specification and shown in the drawings. For example, the detectable elements on the garment may comprise buttons. The marker intended for holding in a hand may have a pistol grip.

Exemplary Computer Platform

Figure 5:
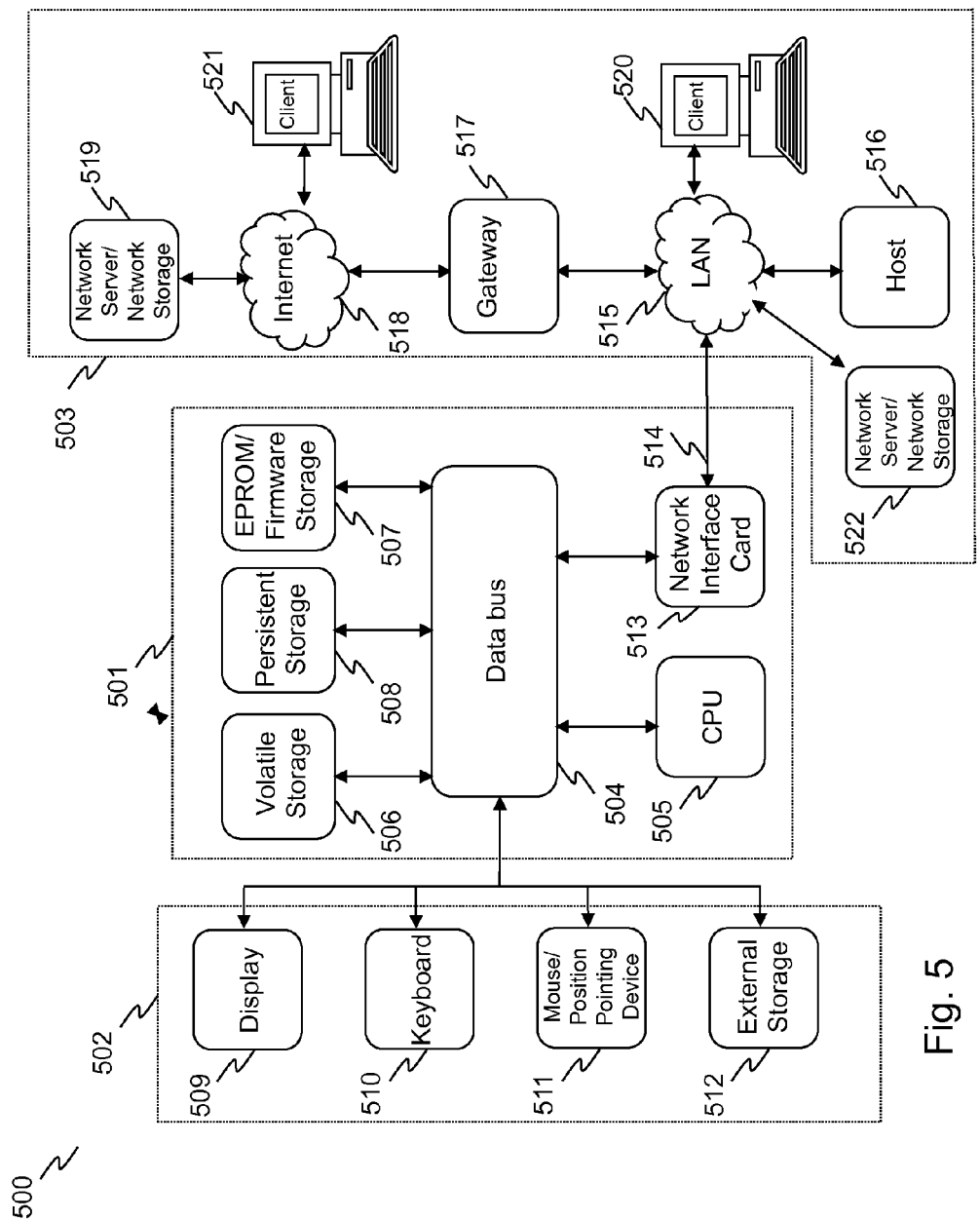
FIG. 5 illustrates an exemplary embodiment of a computer platform upon which the inventive system may be implemented.

FIG. 5 is a block diagram that illustrates an embodiment of a computer/server system 500 upon which an embodiment of the inventive methodology may be implemented. The system 500 includes a computer/server platform 501, peripheral devices 502 and network resources 503.

The computer platform 501 may include a data bus 505 or other communication mechanism for communicating information across and among various parts of the computer platform 501, and a processor 505 coupled with bus 501 for processing information and performing other computational and control tasks. Computer platform 501 also includes a volatile storage 506, such as a random access memory (RAM) or other dynamic storage device, coupled to bus 505 for storing various information as well as instructions to be executed by processor 505. The volatile storage 506 also may be used for storing temporary variables or other intermediate information during execution of instructions by processor 505. Computer platform 501 may further include a read only memory (ROM or EPROM) 507 or other static storage device coupled to bus 504 for storing static information and instructions for processor 505, such as basic input-output system (BIOS), as well as various system configuration parameters. A persistent storage device 508, such as a magnetic disk, optical disk, or solid-state flash memory device is provided and coupled to bus 501 for storing information and instructions.

Computer platform 501 may be coupled via bus 505 to a display 509, such as a cathode ray tube (CRT), plasma display, or a liquid crystal display (LCD), for displaying information to a system administrator or user of the computer platform 501. An input device 510, including alphanumeric and other keys, is coupled to bus 501 for communicating information and command selections to processor 505. Another type of user input device is cursor control device 511, such as a mouse, a trackball, or cursor direction keys for communicating direction information and command selections to processor 505 and for controlling cursor movement on display 509. This input device typically has two degrees of freedom in two axes, a first axis (e.g., x) and a second axis (e.g., y), that allows the device to specify positions in a plane.

An external storage device 512 may be coupled to the computer platform 501 via bus 505 to provide an extra or removable storage capacity for the computer platform 501. In an embodiment of the computer system 500, the external removable storage device 512 may be used to facilitate exchange of data with other computer systems.

The invention is related to the use of computer system 500 for implementing the techniques described herein. In an embodiment, the inventive system may reside on a machine such as computer platform 501. According to one embodiment of the invention, the techniques described herein are performed by computer system 500 in response to processor 505 executing one or more sequences of one or more instructions contained in the volatile memory 506. Such instructions may be read into volatile memory 506 from another computer-readable medium, such as persistent storage device 508. Execution of the sequences of instructions contained in the volatile memory 506 causes processor 505 to perform the process steps described herein. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 505 for execution. The computer-readable medium is just one example of a machine-readable medium, which may carry instructions for implementing any of the methods and/or techniques described herein. Such a medium may take many forms, including but not limited to, non-volatile media and volatile media. Non-volatile media includes, for example, optical or magnetic disks, such as storage device 508. Volatile media includes dynamic memory, such as volatile storage 506.

Common forms of computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, an EPROM, a FLASH-EPROM, a flash drive, a memory card, any other memory chip or cartridge, or any other medium from which a computer can read.

Various forms of computer readable media may be involved in carrying one or more sequences of one or more instructions to processor 505 for execution. For example, the instructions may initially be carried on a magnetic disk from a remote computer. Alternatively, a remote computer can load the instructions into its dynamic memory and send the instructions over a telephone line using a modem. A modem local to computer system can receive the data on the telephone line and use an infra-red transmitter to convert the data to an infra-red signal. An infra-red detector can receive the data carried in the infra-red signal and appropriate circuitry can place the data on the data bus 505. The bus 505 carries the data to the volatile storage 506, from which processor 505 retrieves and executes the instructions. The instructions received by the volatile memory 506 may optionally be stored on persistent storage device 508 either before or after execution by processor 505. The instructions may also be downloaded into the computer platform 501 via Internet using a variety of network data communication protocols well known in the art.

The computer platform 501 also includes a communication interface, such as network interface card 513 coupled to the data bus 505. Communication interface 513 provides a two-way data communication coupling to a network link 515 that is coupled to a local network 515. For example, communication interface 513 may be an integrated services digital network (ISDN) card or a modem to provide a data communication connection to a corresponding type of telephone line. As another example, communication interface 513 may be a local area network interface card (LAN NIC) to provide a data communication connection to a compatible LAN. Wireless links, such as well-known 802.11a, 802.11b, 802.11g and Bluetooth may also used for network implementation. In any such implementation, communication interface 513 sends and receives electrical, electromagnetic or optical signals that carry digital data streams representing various types of information.

Network link 515 typically provides data communication through one or more networks to other network resources. For example, network link 515 may provide a connection through local network 515 to a host computer 516, or a network storage/server 517. Additionally or alternatively, the network link 515 may connect through gateway/firewall 517 to the wide-area or global network 518, such as an Internet. Thus, the computer platform 501 can access network resources located anywhere on the Internet 518, such as a remote network storage/server 519. On the other hand, the computer platform 501 may also be accessed by clients located anywhere on the local area network 515 and/or the Internet 518. The network clients 520 and 521 may themselves be implemented based on the computer platform similar to the platform 501.

Local network 515 and the Internet 518 both use electrical, electromagnetic or optical signals that carry digital data streams. The signals through the various networks and the signals on network link 515 and through communication interface 513, which carry the digital data to and from computer platform 501, are exemplary forms of carrier waves transporting the information.

Computer platform 501 can send messages and receive data, including program code, through the variety of network(s) including Internet 518 and LAN 515, network link 515 and communication interface 513. In the Internet example, when the system 501 acts as a network server, it might transmit a requested code or data for an application program running on client(s) 520 and/or 521 through Internet 518, gateway/firewall 517, local area network 515 and communication interface 513. Similarly, it may receive code from other network resources.

The received code may be executed by processor 505 as it is received, and/or stored in persistent or volatile storage devices 508 and 506, respectively, or other non-volatile storage for later execution.

Finally, it should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein. The present invention has been described in relation to particular examples, which are intended in all respects to be illustrative rather than restrictive. Those skilled in the art will appreciate that many different combinations of hardware, software, and firmware will be suitable for practicing the present invention. For example, the described software may be implemented in a wide variety of programming or scripting languages, such as Assembler, C/C++, perl, shell, PHP, Java, etc.

Moreover, other implementations of the invention will be apparent to those skilled in the art from consideration of the specification and practice of the invention disclosed herein. Various aspects and/or components of the described embodiments may be used singly or in any combination in the systems and methods for virtually displaying real movements of objects in a 3D-space by means of 2D-video capture. It is intended that the specification and examples be considered as exemplary only, with a true scope and spirit of the invention being indicated by the following claims.

What is claimed is:

1. A computer-implemented method for virtually displaying real movements of objects in a 3D-space by means of 2D-video capture, the method being performed in connection with a system comprising: at least a first marker and a second marker, both markers having detectable elements laying in planes; a web camera that has a visual matrix visual matrix sensor that detects the detectable elements for creating a 2D video capture information about movements of said first marker and second marker, the visual matrix visual matrix sensor having a visual matrix having a plane with a pixel coordinate system onto which the images of the detectable elements are projected; a display having a display screen with an image of at least one target; and a central processing unit that communicates with the web camera and with the display and that processes the 2D capture information into 3D video capture signals, the method comprising:

providing an object having at least a first part having a predetermined mobility and a second part having greater mobility than the predetermined mobility of the first part, both parts being independently moveable;

allocating a first marker on the first part and the second marker on the second part of the object;

arranging the first part and the second part in positions where the first marker and the second marker fall into the vision field of the web camera;

moving the first part and a second part with respective markers in space in an $X_1$, $Y_1$, $Z_1$ coordinate system, where axes $X_1$ and $Y_1$ form an $X_1$-$Y_1$ plane parallel to the plane of the respective marker, and axis $Z_1$ is directed from the $X_1$-$Y_1$ plane toward the visual matrix sensor of the web camera;

performing video catching of the movements of the first marker and of the second marker by detecting the detectable elements of the first marker and the second marker thus producing video catching information;

sending the video catching information to the central processing unit and processing the video catching information by converting the movement of the first marker and the second marker into movement of a single cursor on the display;

moving the parts of the object with markers for placing the cursor to a desired position relative to the target;

selecting an arbitrary point on each marker as a point of marker that is in a constant position relative to the marker and the detectable elements of the marker; assuming the center of the visual matrix as a center point of the matrix for subsequent calculations; determining pixel coordinates of the point of marker relative to the center point of the visual matrix; sending the obtained pixel coordinates of the point of marker from the visual matrix to the central processing unit for calculating the coordinates of the point of marker with the use of the algorithm and with a predetermined frequency thus obtaining the trajectories of movement of the points of markers in the pixel coordinates of the visual matrix; using the pixel coordinate system of the visual matrix as a common coordinate system; forming motion vectors from the center point of the matrix coordinate system to the current point on the trajectory of movement of the points of markers; summing the motion vectors of the points of markers into a common vector; and assigning the movement of the common vector to the cursor on the screen of the display so that the movements of the first and the second markers are presented on the screen of the display as movements of the cursor relative to the target; and wherein at least one marker has at least three detectable elements located in predetermined positions unchangeable with respect to the marker so that when the respective marker moves in the direction of axis Z1 the distances between the detectable elements projected onto the visual matrix change, and these changes are used for determining coordinates of the marker on the Z1 axis; and when the marker is turned from the X1-Y1 plane, the distances between the detectable elements in the visual matrix change and these changes can be presented as turns of the marker from the X1-Y1 plane.

2. The computer-implemented method according to claim 1, wherein the object is a human being having a visual channel that obtains visual information and a channel of a muscle-joint sense, the first part is a body part other than a hand, and second part is a hand, the human being selected based on specificity of a movements of body parts as a reaction of the muscle-joint sense in response to the visual information obtained through the visual channel.

3. The computer-implemented method according to claim 2, wherein the first marker comprises at least one detectable element, and the second marker comprises at least three detectable elements.

4. The computer-implemented method according to claim 3, comprising a step of selecting detectable elements from the group consisting of a light source, a mirror, a characteristic part of a human body, a characteristic part of a human garment, and a characteristic object attached to a human garment.

5. The computer-implemented method according to claim 1, wherein in the course of the movement of the markers the pixel coordinates of the detectable elements of each marker on the visual matrix are associated with a X, Y, Z system, where the axes X and Y lay in the matrix plane, and the axis Z is perpendicular to the X-Y plane and has the same scale as the scale on the axes X and Y.

6. A computer-implemented method for virtually displaying real movements of an individual having a first body part of a predetermined mobility and a second body part having mobility higher than the predetermined mobility of the first body part, the individual performing real movements in a 3D-space, the method being performed in connection with a system comprising: at least a first marker and a second marker, both markers having detectable elements located on each marker in predetermined positions unchangeable with respect to the marker; a web camera that has a visual matrix sensor that detects the detectable elements for creating a 2D video capture information about movements of said first marker and second marker, the visual matrix sensor having a visual matrix having a plane with a pixel coordinate system onto which the images of the detectable elements are projected; a display having a display screen with an image of at least one target; and a central processing unit that communicates with the web camera and with the display and that processes the 2D capture information into 3D video capture signals, the method comprising:

providing allocating the first marker on the first part and the second marker on the second part of the individual;

arranging the first part and the second part in positions where the first marker and the second marker fall into the vision field of the web camera;

moving the first body part and a second body part with respective markers in space in an $X_1, Y_1, Z_1$ coordinate system, where axes $X_1$ and $Y_1$ form an $X_1$-$Y_1$ plane parallel to the plane of the respective marker, and axis $Z_1$ is directed from the $X_1$-$Y_1$ plane toward the visual matrix sensor of the web camera;

performing video catching of the movements of the first marker and of the second marker by detecting the detectable elements of the first marker and the second marker thus producing video catching information;

sending the video catching information to the central processing unit and processing the video catching information by converting the movement of the first marker and the second marker into movement of a single cursor on the display;

moving the parts of the object with markers for placing the cursor to a desired position relative to the target;

selecting an arbitrary point on each marker as a point of marker that is in a constant position relative to the marker and the detectable elements of the marker; assuming the center of the visual matrix as a center point of the matrix for subsequent calculations; determining pixel coordinates of the point of marker relative to the center point of the visual matrix; sending the obtained pixel coordinates of the point of marker from the visual matrix to the central processing unit for calculating the coordinates of the point of marker with the use of the algorithm and with a predetermined frequency thus obtaining the trajectories of movement of the points of markers in the pixel coordinates of the visual matrix; using the pixel coordinate system of the visual matrix as a common coordinate system; forming motion vectors from the center point of the matrix coordinate system to the current point on the trajectory of movement of the points of markers; summing the motion vectors of the points of markers into a common vector; and assigning the movement of the common vector to the cursor on the screen of the display so that the movements of the first and the second markers are presented on the screen of the display as movements of the cursor relative to the target; and wherein at least one marker has at least three detectable elements located in predetermined positions unchangeable with respect to the marker so that when the respective marker moves in the direction of axis Z1 the distances between the detectable elements projected onto the visual matrix change, and these changes are used for determining coordinates of the marker on the Z1 axis; and when the marker is turned from the X1-Y1 plane, the distances between the detectable elements in the visual matrix change and these changes can be presented as turns of the marker from the X1-Y1 plane.

7. The computer-implemented method according to claim 6, wherein the first body part is a part other than a hand, and a second body part is a hand, the individual is selected based on specificity of a movements of the body parts as a reaction of the muscle-joint sense in response to the visual information obtained through the visual channel.

8. The computer-implemented method according to claim 7, wherein the first marker and the second marker each comprises at least three detectable elements.

9. The computer-implemented method according to claim 8, comprising a step of selecting detectable elements from the group consisting of a light source, a mirror, a characteristic part of a human body, a characteristic part of a human garment, and a characteristic object attachable to a human garment.

10. The computer-implemented method according to claim 6, wherein in the course of the movement of the markers the pixel coordinates of the detectable elements of each marker on the visual matrix are associated with a X, Y, Z system, where the axes X and Y lay in the matrix plane, and the axis Z is perpendicular to the X-Y plane and has the same scale as the scale on the axes X and Y.

* * * * *